United States Patent
Zahlmann et al.

(10) Patent No.: US 7,194,119 B2
(45) Date of Patent: Mar. 20, 2007

(54) METHOD AND SYSTEM FOR RETRIEVING A MEDICAL PICTURE

(75) Inventors: Gudrun Zahlmann, Neumarkt (DE); Volker Schmidt, Erlangen (DE); Siegfried Schneider, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 782 days.

(21) Appl. No.: 10/301,363

(22) Filed: Nov. 21, 2002

(65) Prior Publication Data
US 2004/0101177 A1   May 27, 2004

(51) Int. Cl.
*G06K 9/00*   (2006.01)

(52) U.S. Cl. .................... 382/128; 382/155; 707/104.1

(58) Field of Classification Search ............... 382/103, 382/128, 129–134, 154, 168, 189, 219, 260, 382/274, 305, 106, 203, 232, 270, 276, 155; 707/104.1, 100; 600/437; 378/20, 21
See application file for complete search history.

(56) References Cited

U.S. PATENT DOCUMENTS

| 5,911,139 | A | | 6/1999 | Jain et al. | ....................... 707/3 |
| 5,915,250 | A | * | 6/1999 | Jain et al. | .................... 707/100 |
| 6,032,678 | A | * | 3/2000 | Rottem | ........................ 600/437 |
| 6,470,092 | B1 | * | 10/2002 | Li et al. | ....................... 382/132 |
| 6,611,609 | B1 | * | 8/2003 | Zhu | ........................... 382/103 |
| 6,941,323 | B1 | * | 9/2005 | Galperin | .................. 707/104.1 |

2001/0043729 A1   11/2001   Giger et al.   ................ 382/128

FOREIGN PATENT DOCUMENTS

EP   1 103 900 A2   5/2001

OTHER PUBLICATIONS

Orphanoudakis S C et al "content-based similarity search in geographically distributed repositories of medical images," Comnuterized Medical Imaging and Graphics, Perqamon Press, 20:4 ( 1996-011: DD. 193-207 XP002183641.*
International Search Report Orphanoudakis S C. Et al.: "IC2net: content-based similarity search in geographically distributed repositories of medical images," *Computerized Medical Imaging and Graphics*, Pergamon Press, 20:4 (Jan. 1996); pp. 193-207 XP002183641.
Printout from Website http://www.onjoph.com/modo.
"Hybrid Fuzzy Image Processing For Situation Assessment," Zahlmann et al, IEEE Engineering In Medicine And Biology, Jan./Feb. 2000, pp. 76-83.

* cited by examiner

*Primary Examiner*—Matthew C. Bella
*Assistant Examiner*—Seyed Azarian
(74) *Attorney, Agent, or Firm*—Alexander J. Burke

(57) ABSTRACT

In a method and system for retrieving a medical image from a data base, an image processing algorithm is applied to a first medical image. The result of the applied image processing algorithm to the first medical image is compared with a plurality of results being stored in a data base. Each result of the plurality of results is the result of the image-processing algorithm being applied to each medical image of a plurality of medical images which is stored in the data base. Then, a second medical image belonging to the plurality of medical images is determined and retrieved from the data base, wherein the relevant result is comparable to the relevant result related to the first medical image.

15 Claims, 5 Drawing Sheets

METHOD AND SYSTEM FOR RETRIEVING A MEDICAL PICTURE

BACKGROUND OF THE INVENTION

1. Field of the Invention

The invention relates to a method and a system for retrieving a medical picture from a data base.

2. Description of the Prior Art

A diagnosis for a patient may be based on a medical picture of the patient. The medical picture may be taken with a special medical apparatus, such as an X-ray or a magnetic resonance apparatus, or with a standard camera. A doctor analyzes the medical picture and eventually makes the diagnosis. If the doctor is not sure about her/his decision, then she/he may compare the patient's medical picture with a reference medical picture which, in general, originates from a different patient who was assigned the same diagnosis. If the reference medical picture and the patient's medical picture are comparable, i.e. if both medical pictures show, for instance, similar or comparable abnormalities specific to the diagnosis, then the doctor can be reassured that her/his diagnosis is very likely correct.

In order to obtain the reference medical picture the doctor may consult a special data base. Such a data base is, for example, available for eye related diseases. This data base, the Multimedia Online Database Ophthalmology ("MODO") is maintained by the Online Journal of Ophthalmology and can be contacted over the Internet (http://www.onjoph.com/modo/).

In order to retrieve the reference medical picture the doctor must know the relevant diagnosis a priori. Therefore, if the doctor is not sure about her/his diagnosis or does not know the diagnosis at all, then she/he cannot easily find a reference medical picture which will match the patient's medical picture.

SUMMARY OF THE INVENTION

An objective of the present invention is to provide a method for retrieving a medical picture or image from a data base which will be comparable to a patient's medical picture or image without knowing a diagnosis for the patient.

Another objective of the invention is to provide a system which can be utilized for retrieving a medical picture or image from a data base which will be comparable to a patient's medical picture or image without knowing a diagnosis for the patient.

The first objective is achieved in accordance with the invention in a method for retrieving a medical picture, comprising the steps of: applying an image processing algorithm to a first medical picture and applying the same image processing algorithm to each medical picture of a set of medical pictures which is stored in a data base, comparing the result of the applied image processing algorithm to the first medical picture with each result of the applied image processing algorithm to each medical picture of the set of medical pictures, and retrieving a second medical picture from the data base. The second medical picture belongs to the set of medical pictures and the result of the applied image processing algorithm to the second medical picture is comparable to the result of the applied image processing algorithm to the first medical picture.

According to the inventive method the image processing algorithm is applied to the first medical picture. The first medical picture is, for instance, taken from a patient who will be diagnosed. The first medical picture may be taken with a special medical apparatus, such as an X-ray or a magnetic resonance apparatus, or with a standard camera suitable for taking the first picture. In order to analyze the first medical picture, the image processing algorithm is applied to it. The image processing algorithm is designed, for example, to detect a specific pattern in the first medical picture related to a specific abnormality and thus specific to a certain diagnosis. If, for example, the first medical picture is a picture of the retina of one of the patient's eye, the image processing algorithm is designed to detect, for instance, lesions which have been developed by the patient and are more or less visible in the first medical picture. Particularly, the image processing algorithm may be designed to detect the number of lesions, the degree of severity of detected lesions, or the type of lesions appearing in the first medical picture. The result of the applied image processing algorithm to the first picture may then be the number, the degree of severity, or the type or types of detected lesions in the first medical picture. Suitable image processing algorithms are specifically pattern recognition algorithms which are notoriously known in the art. Suitable image processing algorithms are, for instance, disclosed in G. Zahlmann, et al, "Hybrid Fuzzy Image Processing For Situation Assessment", IEEE Engineering In Medicine And Biology, January/February 2000, pp. 76–83.

After the image processing algorithm has been applied to the first medical picture, the same image processing algorithm is applied to each medical picture of the set of medical pictures which is stored in the data base. By the way, instead of first applying the image processing algorithm to the first medical picture and then applying the same image processing algorithm to the set of medical picture, the image processing algorithm can also be first applied to the set of medical pictures and then to the first medical picture. Then each result of the applied image processing algorithm to each medical picture of the set of medical pictures is compared with the result of the applied image processing algorithm to the first medical picture. If a result of the applied image processing algorithm to the first medical picture is comparable to the result associated with one medical picture or more medical pictures of the set of medical pictures, then this medical picture is the second medical picture which is, according to the inventive method, retrieved from the data base. Comparable results are, for instance in the case of medical pictures of an eye, the number, the degree of severity, or the types of detected lesions or pattern related to the lesions.

Consequently, a person to make a diagnosis based on the first medical picture obtains a reference medical picture, the second picture, which in general originates from a different patient who very likely has the same abnormality or disease as the patient who belongs to the first medical picture. Since the person to make the diagnosis knows the second picture he/she may be better prepared to diagnose the patient whose first medical picture is to be evaluated. The person to diagnose may be an ophthalmologist, if the first picture is a picture of an eye, or in general a medical doctor or practitioner. The person to diagnose, however, may also be a person with only little or none medical background, such as graders who evaluate medical pictures during a medical screening.

The person to diagnose has an improved chance to make a better diagnosis, if, as it is planned in according with different embodiments of the inventive method, the second medical picture with its relevant result, after being retrieved from the data base, is displayed on a screen, the relevant result of the first medical image is displayed, or the relevant results related to both, the first medical picture and the second medical picture, are displayed.

The person to diagnose the patient based on the first medical picture may further be supported in her/his decision, if, in accordance to a further restricted embodiment of the inventive method, the second medical picture is displayed with an information of a diagnosis associated with the second medical picture. This information is also stored in the data base.

In another restricted embodiment of the inventive method, a region of interest is determined in the first medical picture, so that the image processing algorithm is applied to that region of interest.

The first objective is also achieved in accordance with the invention in a method for retrieving a medical image from a data base, comprising the steps of: applying an image processing algorithm to a first medical image and comparing the result of the applied image processing algorithm to the first medical image with a plurality of results which is stored in a data base; each result of the plurality of results is the result of the image processing algorithm applied to each medical image of a plurality of medical images which is stored in said data base. After the comparison, a second medical image belonging to the plurality of medical images is determined, wherein the result of the image processing algorithm applied to the second medical image is comparable to the result of the image processing algorithm applied to the first medical image. Finally, the second medical image is retrieved from the data base.

The inventive method utilizes the data base in which the plurality of medical images and the plurality of results are stored. Each result of the plurality of results is the result of an applied image processing algorithm to a medical image of the plurality of medical images. In comparison to the above described inventive method, the relevant results of the applied image processing results are already stored in the data base. Thus the image processing algorithm does not need to be applied to each medical image of the plurality of medical images shortly before or after applied to the first medical image, resulting in a shorter time needed to carry out the second inventive method.

In addition, the invention provides a system comprising a data processing unit and a data base operatively coupled to the data processing unit. The data processing unit is configured to store a first medical image, to apply an image processing algorithm to the first medical image, and to obtain a first result due to the applied image processing algorithm to the first medical image. The data base comprises a plurality of medical images and a plurality of results; each result of the plurality of results is the result of the image processing algorithm applied to each medical image of the plurality of medical images. The data processing unit is further configured to compare the first result with each result of the plurality of results and to retrieve a second medical image from the data base. The second medical image belongs to the plurality of images and the result of the image processing algorithm applied to the second medical image is comparable to the first result.

In a more restricted embodiment of the inventive system, the data processing unit is configured to retrieve, in addition to the second medical image, the result of the image processing algorithm applied to the second medical image.

In a further more restricted embodiment of the system according to the invention, the data base has an information for each medical image of the plurality of medical images about a diagnosis associated with each medical image of the plurality of medical images and the data processing is configured to retrieve, in addition to the second medical image, its relevant information about its related diagnosis.

DESCRIPTION OF THE PREFERRED EMBODIMENTS

Figure 1:
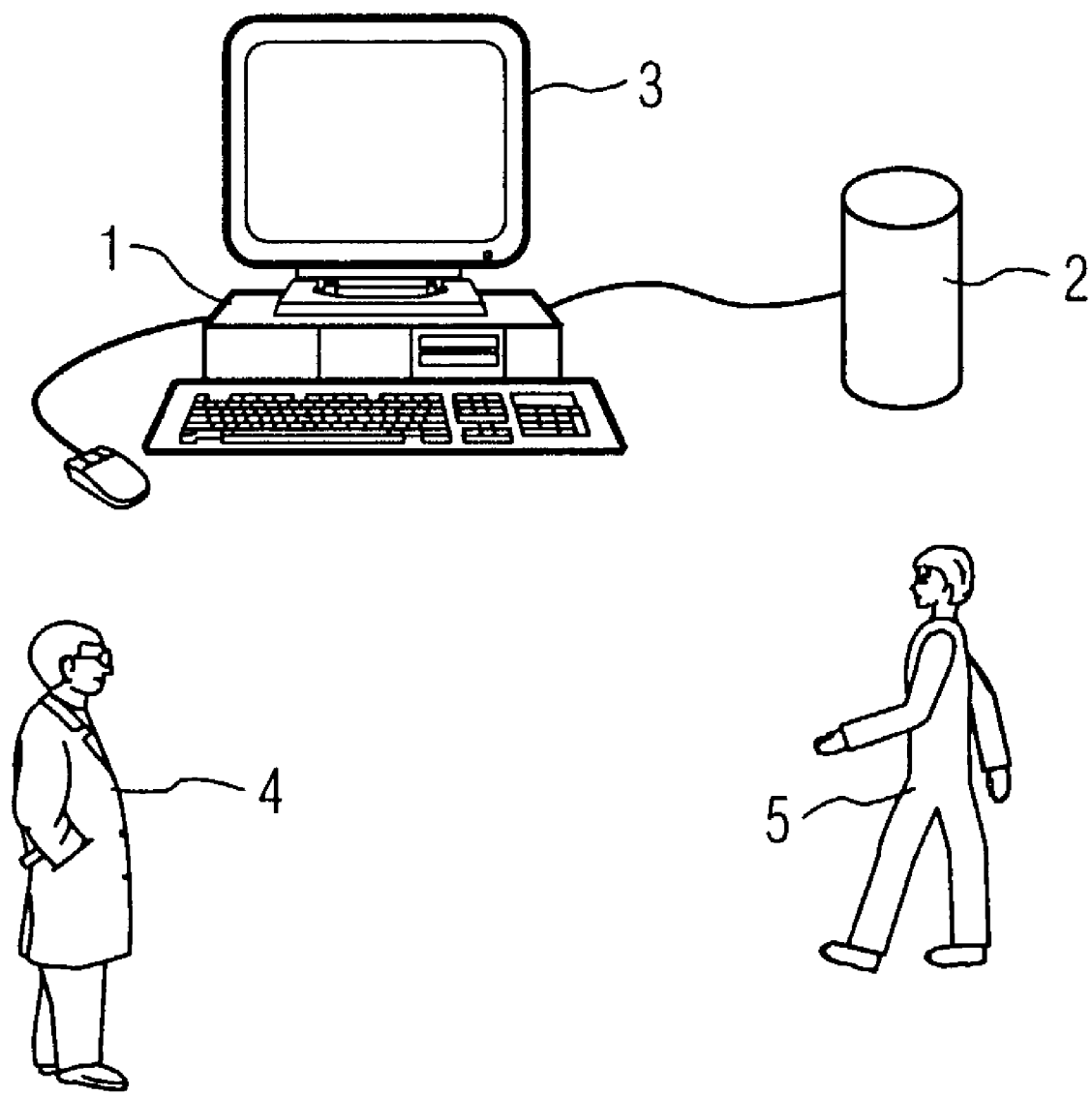
FIG. 1 shows a scenario illustrating the invention.

FIG. 1 illustrates an exemplary scenario of the inventive system. The system comprises a computer 1 which is operatively coupled to a data base 2. The data base 2 may be connected directly to the computer 1, as shown in FIG. 1. Data base 2, however, can also be a part of computer 1 or indirectly connected to computer 1, for instance, through a information network, such as the Internet. Data base 2 comprises a plurality of medical images including their relevant diagnosis.

Computer 1 is further configured to store, at least temporarily, a medical image and to display it on a screen 3 which is connected to computer 1. In addition, computer 1 is configured with one or more image processing algorithms which can be applied to that medical image. The image processing algorithm is designed to recognize a certain pattern of the medical image. If the medical image is, for instance, the image of a patient's eye, then the image processing algorithm may be designed to detect lesions of the eye. Typical lesions are microaneurysms (MA), haemorrhages (HAEM), hard exudates plus their location in relation to the temporal arcade (HE), maculopathy, cotton wool spots (CWS), and intra-retinal microvascular abnormalities (IRMA). Suitable image processing algorithms are pattern recognition algorithms which are notoriously known in the art and thus are not further described. A suitable image processing algorithm is, for example, disclosed in G. Zahlmann, et al, "Hybrid Fuzzy Image Processing For Situation Assessment", IEEE Engineering In Medicine And Biology, January/February 2000, pp. 76–83.

Figure 2:
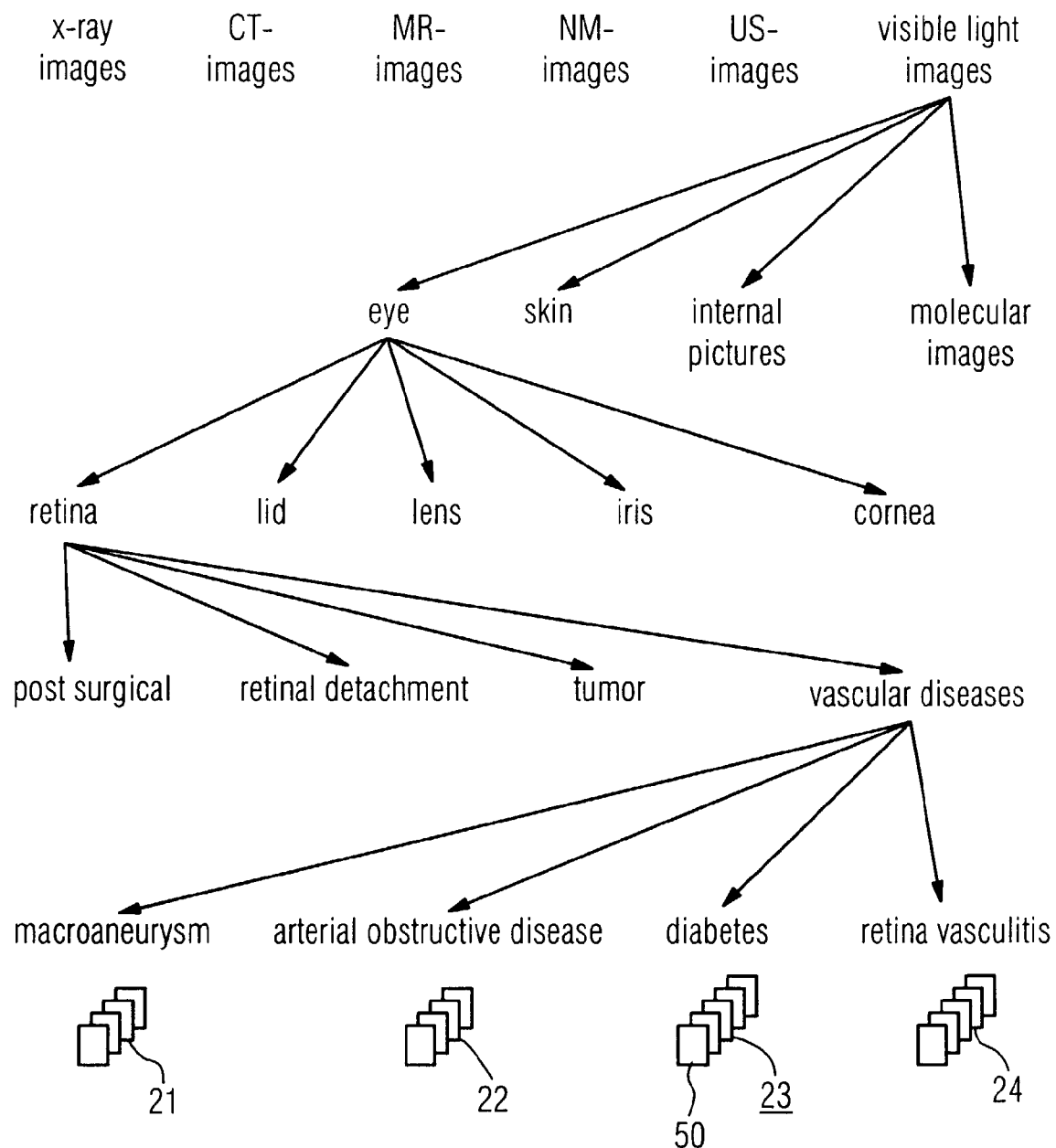
FIG. 2 shows the structure of a data base.

A structure of data base 2 is illustrated in FIG. 2 as an example. Data base 2 comprises a plurality of medical images. The medical images are categorized as "X-ray images", "computed tomography (CT) images", "magnetic resonance (MR) images", "nuclear medicine (NM) images", "ultrasound (US) images", and "visible light images". The visible light images are taken with a standard camera which may be adapted for medical purposes. Each type of medical image is further categorized in more detail. Nevertheless, in FIG. 2 only the category of visible light images is shown in more detail. For this example, the visible light images are further categorized according to different parts of a human body, such as "eye", "skin", "internal pictures", and "molecular images". Each of that sub-category is further divided. In order not to overload FIG. 2, only the sub-category of visible light images of an eye is illustrated. For this exemplary embodiment, the visible light images of an eye are categorized into "retina", lid", "lens", "iris", and "cornea". Each of this sub-category is again divided while only the division of visible light images of the retina is illustrated in FIG. 2. Visible light images of the retina are divided into different diseases or abnormalities affecting the retina. For this exemplary embodiment, the visible light images of the retina are categorized into "post-surgical", "retinal detachment", "tumor", and "vascular diseases". Each of that sub-category is further divided while only the division of vascular diseases of the retina are illustrated in more detail. Vascular diseases are categorized as "macroaneurysm", "arterial obstructive disease", "diabetes", and "retinal vasculitis", for this example. For each of those categories is one or more related visible light images including a description of the relevant diagnosis stored. For this exemplary embodiment, a set of visible light images 21 including their relevant diagnoses is shown for the category "macroaneurysm", a set of visible light images 22 including their relevant diagnoses is shown for the category "arterial obstructive disease", a set of visible light images 23 including their relevant diagnoses is shown for the category "diabetes", and a set of visible light images 24 including their relevant diagnoses is shown for the category "retinal vasculitis".

For this exemplary embodiment, each medical image of data base 2 was also applied with an image processing algorithm which detects specific patterns related to certain abnormalities or diseases associated with that medical image. For example, the set of visible light images 23 related to images of an eye of patients having diabetes were applied with an image processing algorithm which is designed to detect patterns typical for lesions. This image processing algorithm searches in particular for lesions such as microaneurysms (MA), haemorrhages (HAEM), hard exudates plus their location in relation to the temporal arcade (HE), maculopathy, cotton wool spots (CWS), and intra-retinal microvascular abnormalities (IRMA). Each type of lesion has a specific pattern. Cotton wool spots (CWS), for instance, are characterized by fluffy white spots detectable in an image of an eye's retina and superficial intraretinal hemorrhages are characterizes by dark lines including dark spots.

The results of each applied image processing algorithm to each of the medical images stored in data base 2 are stored with its relevant medical image. In addition to that information, there is also stored in the data base 2 an information about a diagnosis related to each of the medical images.

Figure 3:
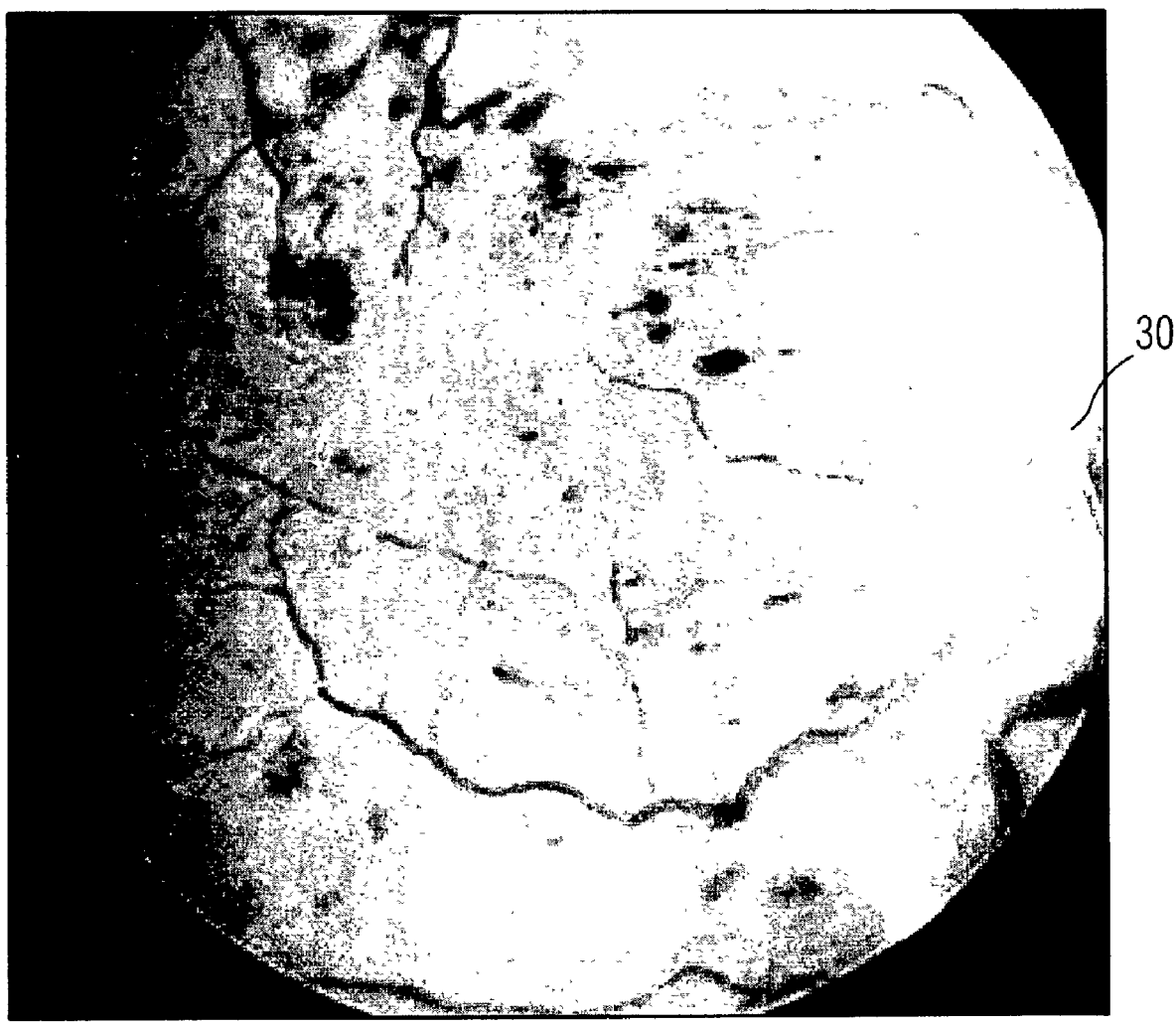
FIG. 3 shows a medical image of a patient's eye.

In the exemplary embodiment, an ophthalmologist 4 uses the computer 1 to evaluate a medical image 30 which is shown in FIG. 3. For the present example, the medical image 30 is taken from a patient 5. In order to evaluate the medical image 30, the medical image 30 is stored on computer 1 and is displayed on the screen 3 which is connected to computer 1. In the present example, the ophthalmologist 4 wants to make a diagnosis for the patient 5 based on the medical image 30. Generally, the computer 1 can be used by any person who wants to evaluate a medical image. As a result, this person does not need to be an ophthalmologist 4 or, in general, a medical practitioner. This person can especially be a grader evaluating medical images during a medical screening.

After the medical image 30 is displayed on the screen 3, the ophthalmologist 4 applies an image processing algorithm to the medical image 30. The applied image processing algorithm searches in this example for lesions appearing in the medical image 30 and particularly for microaneurysms (MA), haemorrhages (HAEM), hard exudates plus their location in relation to the temporal arcade (HE), maculopathy, cotton wool spots (CWS), and intra-retinal microvascular abnormalities (IRMA). As a result, the image processing algorithm searches for patterns associated with each of the different lesions.

Figure 4:
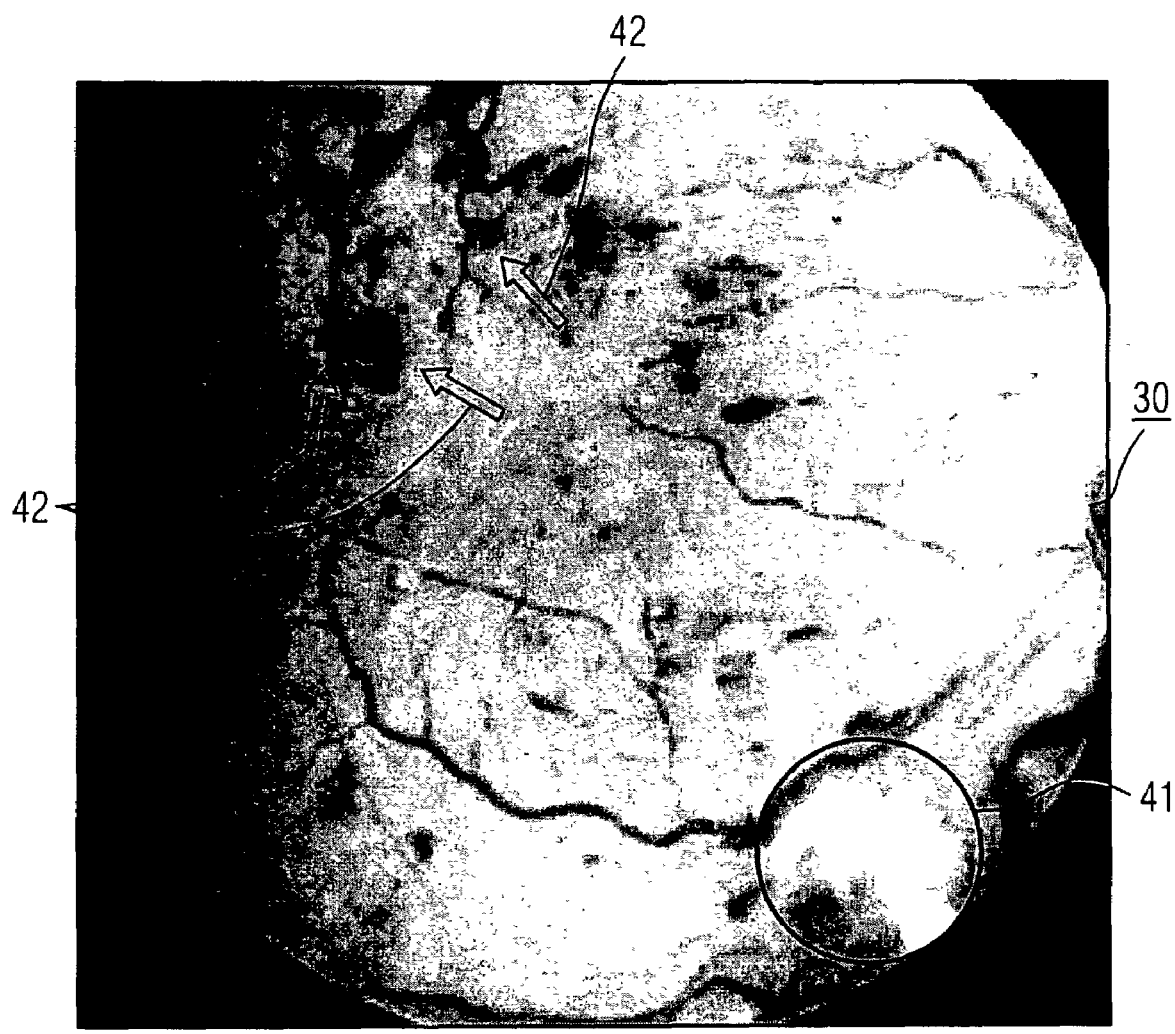
FIG. 4 shows the medical image of FIG. 2 including the result of an applied image processing algorithm to the first medical image.

In this particular case, the image processing algorithm detects fluffy white spots and a few dark lines with dark spots. The fluffy white spots are marked by a circle 41 and the dark spots are emphasized by little arrows 42 which are inserted in the medical image 30 as shown in FIG. 4.

After that, a computer program running on computer 1 automatically compares the result of the applied image processing algorithm to the medical image 30 with the results of applied image processing algorithms to the medical images stored in data base 2. In this case, the computer program searches in particular for results indicating dark lines with dark spots and fluffy white spots in a medical image of an eye. If the computer program finds such a result, then it considers the result of the applied image processing algorithm to the medical image 30 as comparable to the found result and retrieves the related medical image including its relevant result and diagnosis from the data base 2.

Figure 5:
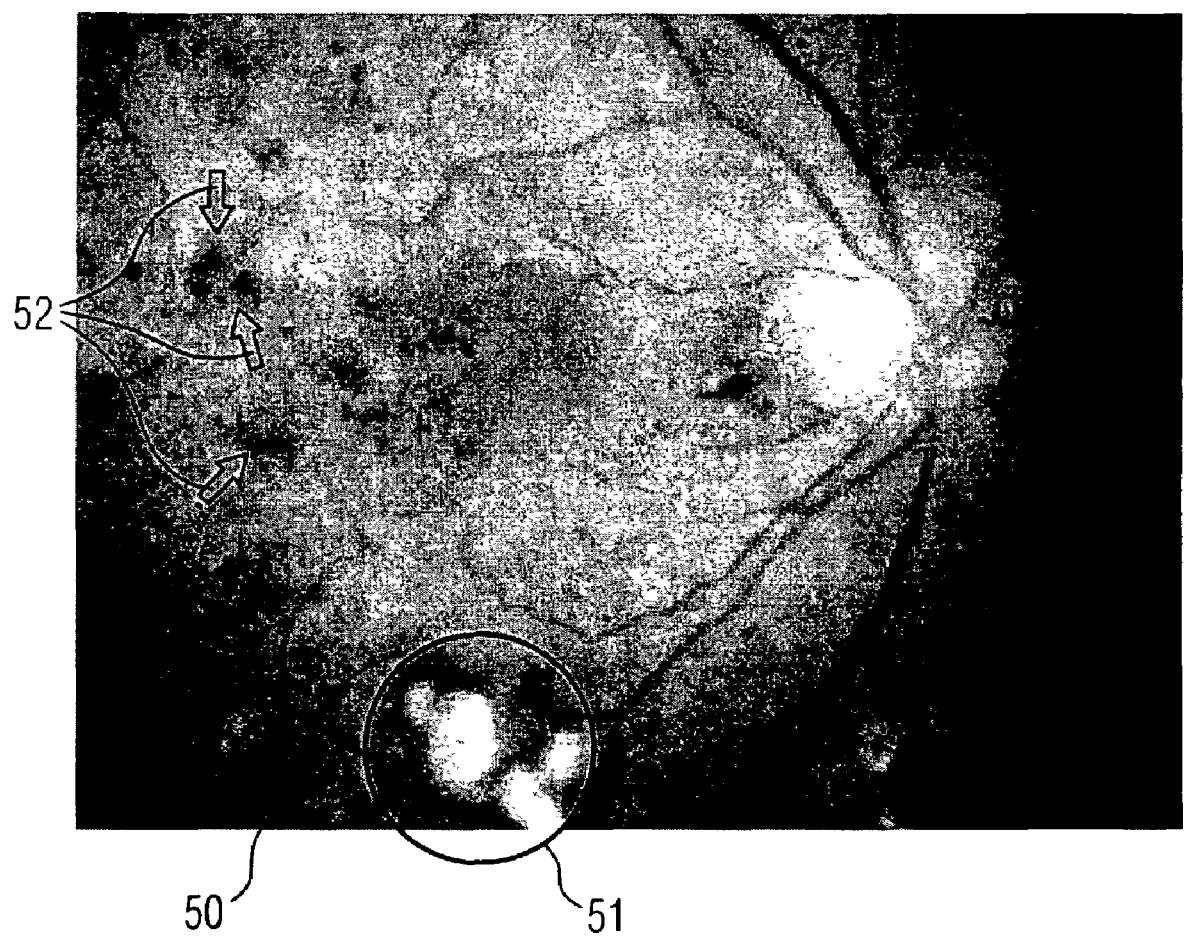
FIG. 5 shows a medical image which is stored in the data base depicted in FIG. 2 including information about the second medical image.

In this example, the computer program detects such a result stored in data base 2. This result relates to a visible light image 50. The visible light image 50 which is shown in more detail in FIG. 5 is an image of an eye having fluffy white spots (cotton wool spots) indicating microinfarcts and dark lines with dark spots representing blood vessels with superficial intraretinal hemorrhages. Consequently, the computer program retrieves the visible light image 50 including the result of the applied image processing algorithm and the related diagnosis from the data base 2 and displays them on the screen 3. The fluffy with spots are marked with a circle 51 and the dark lines with dark spots are emphasized by arrows 52. For this example, the visible light image 50 originates from a patient (not shown in the Figures) who is different from patient 5.

Since the ophthalmologist 4 obtains the visible light image 50 including the result of the applied image processing algorithm and the diagnosis related to the visible light image 50, she/he can compare the visible light image 50 with the medical image 30. This comparison can support the ophthalmologist 4 to make a diagnosis for the patient 5.

For an alternative embodiment of the invention, a scenario similar to that shown in FIG. 1 is used. For the alternative embodiment, however, the data base 2 does not comprise an information about an applied image processing algorithm to the medical images stored in data base 2.

Similar to the above described embodiment, computer 1 is configured with the image processing algorithm which is described above and can be applied to a medical image which is, at least temporarily, stored on computer 1. After starting the computer program, this image processing algorithm analyzes the medical image, such as the medical image 30, as described above. The computer program is further designed to apply this image processing algorithm to each of the medical images stored in the data base 2 and to compare each of the results with the result of the applied image processing algorithm to the medical image 30. Since the results of the applied image processing algorithm to the medical image 30 and to the visible light image 50 are comparable, the computer 1 retrieves the visible light image 50 from data base 2 with its related diagnosis and displays the visible light image 50 with its related diagnosis and the relevant result of the applied image processing algorithm on the screen 3.

Instead of applying the signal processing algorithm to the entire medical image 30, the ophthalmologist 4 can mark a region of interest 31 in the medical image 30, for instance with the mouse of computer 1. Then, the image processing algorithm is only applied to that region of interest 31.

Even though the invention is described for medical pictures of an eye, the invention is in general applicable for all kinds of medical pictures and particularly to X-ray images obtained for mammography.

Instead of applying the signal processing algorithm to the entire medical image 30, the ophthalmologist 4 can mark a region of interest 31 in the medical image 30, for instance with the mouse of computer 1. Then, the image processing algorithm is only applied to that region of interest 31.

Even though the invention is described for medical pictures of an eye, the invention is in general applicable for all kinds of medical pictures and particularly to X-ray images obtained for mammography.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for retrieving a medical picture, comprising the steps of:
    applying an image processing algorithm to a region of interest in a first medical picture for searching for a plurality of patterns associated with a plurality of diagnoses within said first medical picture to obtain a first processing result;
    applying said image processing algorithm to each medical picture of a set of medical pictures stored in a database to obtain a second processing result, said set not containing said first medical picture;
    comparing the first processing result with each second processing result; and
    retrieving from said database a second medical picture in said set of medical pictures having a second processing result comparable to the first processing result.

2. The method of claim 1, comprising, after retrieving said second medical picture from said database, the step of:
    displaying said second medical picture with its second processing result.

3. The method of claim 1, comprising, after retrieving said second medical picture from said database, the step of:
    displaying the first processing result.

4. The method of claim 1, comprising, after retrieving said second medical picture from said database, the step of:
    displaying said second medical picture with its second processing result and displaying the first processing result.

5. The method of claim 1, comprising, after retrieving said second medical picture from said database, the step of:
    displaying said second medical picture with information of a diagnosis associated with said second medical picture, said information being stored with said second medical picture in said database.

6. The method of claim 1, including the step of:
    determining a region of interest in said first medical picture.

7. A method for retrieving a medical image from a database, comprising the steps of:
    applying an image processing algorithm to a region of interest in a first medical image for searching for a plurality of patterns associated with a plurality of diagnoses within said first medical picture to obtain a first processing result;
    comparing the first processing result with a plurality of second processing results which is stored in a database, each second processing result being a result of said image processing algorithm applied to each medical image of a plurality of medical images, not including said first medical image, which is stored in said database;
    determining a second medical image in said plurality of medical images having a second processing result comparable to the first processing result; and
    retrieving said second medical image from said database.

8. The method of claim 7, comprising, after retrieving said second medical Image from said database, the step of:
    displaying said second medical image with its second processing result.

9. The method of claim 7, comprising, after retrieving said second medical image from said database, the step of:
    displaying the first processing result.

10. The method of claim 7, comprising, after retrieving said second medical image from said database, the step of:
    displaying said second medical image with its second processing result and displaying the first processing result.

11. The method of claim 7, comprising, after retrieving said second medical image from said database, the step of:
    displaying said second medical image with information of a diagnosis associated with said second medical image, said information being stored with said second medical image in said database.

12. The method of claim 7, including the step of:
    determining a region of interest in said first medical image.

13. A system comprising:
    a data processing unit configured to store a first medical image, to apply an image processing algorithm to a region of interest in said first medical image for searching for a plurality of patterns associated with a plurality of diagnoses within said first medical picture, and to obtain a first result due to the applied said image processing algorithm to said first medical image;
    a database operatively coupled to said data processing unit, said database comprising a plurality of medical images, not including said first medical image, and a plurality of second results, each second result in said plurality of results being a result of applying said image processing algorithm to each medical image of said plurality of medical images;
    said data processing unit further being configured to compare said first result with each second result and to retrieve a second medical image from said database from among said plurality of images having a second result comparable to said first result.

14. The system of claim 13, wherein:
    said data processing unit is configured to retrieve, in addition to said second medical image, the second result for said second medical image.

15. The system of claim 13, wherein:
    said database contains, for each medical image of said plurality of medical images information about a diagnosis associated with each medical image of said plurality of medical images; and
    said data processing being configured to retrieve, in addition to said second medical image, the information associated therewith in said database.

\* \* \* \* \*